(12) United States Patent
Kruglick

(10) Patent No.: US 9,784,692 B2
(45) Date of Patent: Oct. 10, 2017

(54) ROADWAY INFRASTRUCTURE MONITORING BASED ON AGGREGATED MOBILE VEHICLE COMMUNICATION PARAMETERS

(71) Applicant: Empire Technology Development LLC, Wilmington, DE (US)

(72) Inventor: Ezekiel Kruglick, Poway, CA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 470 days.

(21) Appl. No.: 14/372,439

(22) PCT Filed: Feb. 7, 2014

(86) PCT No.: PCT/US2014/015322
§ 371 (c)(1),
(2) Date: Jul. 15, 2014

(87) PCT Pub. No.: WO2015/119619
PCT Pub. Date: Aug. 13, 2015

(65) Prior Publication Data
US 2016/0011124 A1 Jan. 14, 2016

(51) Int. Cl.
*G01N 22/00* (2006.01)
*G01C 21/26* (2006.01)

(52) U.S. Cl.
CPC ............. *G01N 22/00* (2013.01); *G01C 21/26* (2013.01)

(58) Field of Classification Search
USPC ................................................ 324/637, 642
See application file for complete search history.

(56) References Cited

U.S. PATENT DOCUMENTS

2005/0065711 A1* 3/2005 Dahlgren ............... G07C 5/008
701/117
2009/0021423 A1 1/2009 Cheng et al.
(Continued)

FOREIGN PATENT DOCUMENTS

EP 1223567 A1 7/2002
WO 2011016857 A2 2/2011

OTHER PUBLICATIONS

"A Bridge Collapses," published on Aug. 5, 2007, Accessed at http://www.nytimes.com/2007/08/05/opinion/05sun1.html?_r=1&, Accessed on Jul. 9, 2014, pp. 2.
(Continued)

*Primary Examiner* — Vincent Q Nguyen
(74) *Attorney, Agent, or Firm* — Turk IP Law, LLC

(57) ABSTRACT

Technologies are generally described to monitor roadway infrastructure based on aggregated mobile vehicle communication parameters. In some examples, a pair of vehicles with mobile communication devices passing an infrastructure, such as a bridge, may be identified, and the mobile communication devices may exchange a signal during a mobile communication as the vehicles pass the target infrastructure. During the signal exchange, channel characterization data for the target infrastructure may be collected. The channel characterization data may represent propagation conditions of signal waves through the target infrastructure. The channel characterization data may be received at a mobile communication network, where a tomographic model of the target infrastructure may be generated based on extraction and analysis of the channel characterization data. Physical and structural characteristics of the target infrastructure may be determined based on the generated tomographic image of the target infrastructure to facilitate monitoring for degradation and flaws in the target infrastructures.

25 Claims, 7 Drawing Sheets

(56) References Cited

U.S. PATENT DOCUMENTS

| | | |
|---|---|---|
| 2011/0095908 A1 | 4/2011 | Nadeem et al. |
| 2011/0187702 A1 | 8/2011 | Schwartz |
| 2011/0273321 A1 | 11/2011 | Joshi et al. |
| 2013/0018575 A1 | 1/2013 | Birken et al. |
| 2013/0030687 A1 | 1/2013 | Shida |
| 2013/0301584 A1 | 11/2013 | Addepalli et al. |

OTHER PUBLICATIONS

"Chapter 4: Inspection Procedures—General Discussion," Accessed at http://web.archive.org/web/20131013011846/http://www.fhwa.dot.gov/bridge/tunnel/inspectman04.cfm, Accessed on Jul. 9, 2014, pp. 24.

"I1 MAGIC," Accessed at http://web.archive.org/web/20131221205227/http://users.ece.gatech.edu/~justin/I1magic/, Accessed on Jul. 9, 2014, pp. 3.

"MIMO Performance and Condition Number in LTE Test," Accessed at http://web.archive.org/web/20140709071341/http://cp.literature.agilent.com/litweb/pdf/5990-4759EN.pdf, Accessed on Jul. 9, 2014, pp. 14.

"Modern Bridge and Infrastructure Inspection Methods and the Need for Faster, More Frequent and Ore Efficient Inspection," on Mar. 7, 2011, Accessed at http://web.archive.org/web/20130810071823/http://nextbigfuture.com/2011/03/modern-bridge-and-infrastructure.html, Accessed on Jul. 9, 2014, pp. 12.

"National Bridge Inventory (NBI)," Accessed at http://web.archive.org/web/20140109110230/http://www.fhwa.dot.gov/bridge/nbi.cfm, Accessed on Jul. 9, 2014, p. 1.

"WiMAX MIMO," Accessed at http://web.archive.org/web/20120508101740/http://en.wikipedia.org/wiki/WiMAX_MIMO, Accessed on Jul. 9, 2014, pp. 8.

Cande's, E. et al., "Robust Uncertainty Principles: Exact Signal Reconstruction from Highly Incomplete Frequency Information," IEEE Trans. Information Theory, vol. 52, No. 2, pp. 489-509, (2006).

International Search Report for International Patent Application No. PCT/US2014/015322 mailed May 19, 2014.

Karedal, J. et al., "A geometry-based stochastic MIMO model for vehicle-to-vehicle communications," IEEE Transactions on Wireless Communications, vol. 8, No. 7, pp. 3646-3657 (2008).

Keel, J., "An Audit Report on the Department of Transportation's Bridge Inspection Program," on Dec. 2009, Accessed at http://web.archive.org/web/20131118142730/http://www.sao.state.tx.us/reports/report.aspx?reportnumber=10-017, Accessed on Jul. 9, 2014, pp. 2.

Leber, J., "How Wireless Carriers are Monetizing Your Movements," Accessed at http://www.technologyreview.com/news/513016/how-wireless-carriers-are-monetizing-your-movements/, Accessed on Jul. 9, 2014, pp. 4.

Lee, J. et al., "MIMO Technologies in 3GPP LTE and LTE-Advanced," EURASIP Journal on Wireless Communications and Networking, vol. 2009, No. 3, pp. 10 (2009).

Luettel, T. et al., "Autonomous Ground Vehicles-Concepts and a Path to the Future," Proceedings of the IEEE 100 (Centennial-Issue), pp. 1831-1839, May 2012.

Mandache, C., and Lefebvre, J. H. V., "Electromagnetic enhancement of pulsed eddy current signals", AIP Conference Proceedings, vol. 894, pp. 318-324, (2007).

Mostofi, Y., "Cooperative Wireless-Based Obstacle/Object Mapping and See-Through Capabilities in Robotic Networks," IEEE Transactions on Mobile Computing, vol. 12, No. 5, May 2013, pp. 817-829.

Murner, C. and Hansen, J. P., "Buried Corrosion Detection in Multi-Layer Airframe Structures Using Pulsed Eddy Current", 17th World Conference on NondestructiveTesting, Shanghai, China, Oct. 25-28, 2008, pp. 7.

Pätzold, M. and Hogstad, B. O., "A wideband MIMO channel model derived from the geometric elliptical scattering model," Wireless Communications & Mobile Computing, vol. 8, No. 5, pp. 138-143, Sep. 2006.

Reid, R. L., "The Infrastructure Crisis," Accessed at http://www.asce.org/Content.aspx?id=25562, Accessed on Jul. 9, 2014, pp. 27.

Salmi, J. et al., "Detection and tracking of MIMO propagation path parameters using state-space approach," IEEE Transactions on Signal Processing, vol. 57, No. 4, pp. 1538-1550 (2009).

Thrun, S., "Artificial intelligence for robotics," Accessed at http://web.archive.org/web/20140122074921/https://www.udacity.com/course/cs373, Accessed on Jul. 9, 2014, pp. 3.

Washer, G. A., "Developing NDE Technologies for Infrastructure Assessment," Accessed at http://web.archive.org/web/20111022120327/https://www.fhwa.dot.gov/publications/publicroads/00jan/nde.cfm, Accessed on Jul. 9, 2014, pp. 7.

Wicks, M.C., "RF Tomography with Application to Ground Penetrating Radar," Proc. Asilomar Conf. Signals, Systems and Computers, Nov. 2007, pp. 2017-2022.

Wilson, J., and Patwari, N., "Radio Tomographic Imaging with Wireless Networks," IEEE Transactions on Mobile Computing, vol. 9, No. 5, pp. 621-632 (2010).

Xiaoduan, S. et al., "Analysis of Past National Bridge Inventory Ratings for Predicting Bridge System Preservation Needs." Transportation Research Record, vol. 1866, No. 1, Jan. 1, 2004, pp. 36-43.

Yu, K. and Ottersten, B., "Models for MIMO propagation channels: a review," Wireless Communications and Mobile Computing, vol. 2, No. 7, pp. 653-666 (2002).

* cited by examiner

ROADWAY INFRASTRUCTURE MONITORING BASED ON AGGREGATED MOBILE VEHICLE COMMUNICATION PARAMETERS

CROSS-REFERENCE TO RELATED APPLICATION

This Application is the U.S. National Stage filing under 35 U.S.C. §371 of International Application No. PCT/US14/15322 filed on Feb. 7, 2014. International Application No. PCT/US14/15322 is hereby incorporated by reference in its entirety.

BACKGROUND

Unless otherwise indicated herein, the materials described in this section are not prior art to the claims in this application and are not admitted to be prior art by inclusion in this section.

Monitoring and inspection of roadway infrastructure, such as bridges, tunnels, pillars, and overpasses, is important in order to detect structural flaws, such as corrosion and degradation, in order to improve and maintain the integrity and safety of the infrastructures. Degradation of roadway infrastructures is generally a continuous process, and continuous and increased inspection frequency may be needed to monitor corrosion and material loss as aging accelerates. Example infrastructure monitoring may entail an in-person inspection by a qualified technician with advanced and expensive equipment, and may consequently be a costly and time-consuming endeavor.

SUMMARY

According to some examples, methods are described to monitor roadway infrastructure based on aggregated mobile vehicle communication parameters. The method may include identifying a target infrastructure to monitor, identifying a pair of mobile communication devices approaching the target infrastructure, instructing the pair of mobile communication devices to communicate with each other through one or more signals as the pair of mobile communication devices pass the target infrastructure, instructing at least one of the pair of mobile communication devices to collect information about the one or more signals, receiving the collected information about the one or more signals from the at least one of the pair of mobile communication devices, and/or analyzing the collected information about the one or more signals to determine a structural characteristic of the target infrastructure.

According to some examples, the present disclosure also describes a controller to monitor roadway infrastructure based on aggregated mobile vehicle communication parameters. The controller may include a memory configured to store instructions, a communication module configured to facilitate communications with one or more mobile communication devices and to instruct the mobile communication devices to exchange one or more signals, and a processor coupled to the memory and the communication module, the processor configured to execute a tomography application in conjunction with the instructions stored in the memory. The tomography application may be configured to identify a target infrastructure for monitoring, identify a pair of mobile communication devices approaching the target infrastructure via a pairing module of the tomography application, control the communication module to instruct the pair of mobile communication devices to communicate with each other through the one or more signals as the pair of mobile communication devices pass the target infrastructure, control the communication module to instruct at least one of the pair of mobile communication devices to collect information about the one or more signals, receive the information about the one or more signals from the at least one of the pair of mobile communication devices, and/or analyze the collected information about the one or more signals to determine a structural characteristic of the target infrastructure.

According to other examples, the present disclosure also describes a mobile communication network to monitor roadway infrastructure based on aggregated mobile vehicle communication parameters. The mobile communication network may include a plurality of mobile communication devices, and one or more servers to manage communication among the plurality of mobile communication devices, where at least one of the one or more servers may be configured to identify a target infrastructure for monitoring, identify pairs of mobile communication devices approaching the target infrastructure, instruct the pairs of mobile communication devices to communicate with each other through the one or more signals as the pairs of mobile communication devices pass the target infrastructure, instruct one or more of the pairs of mobile communication devices to collect information about the one or more signals, receive the collected information about the one or more signals from the one or more of the pairs of mobile communication devices, aggregate the received information about the one or more signals from the pairs of mobile communication devices that pass the target infrastructure over a period of time, and/or analyze the aggregated information about the one or more signals to determine a structural characteristic of the target infrastructure.

According to yet other examples, the present disclosure describes a computer readable storage medium with instructions stored thereon, which when executed on one or more computing devices execute a method to monitor roadway infrastructure based on aggregated mobile vehicle communication parameters.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
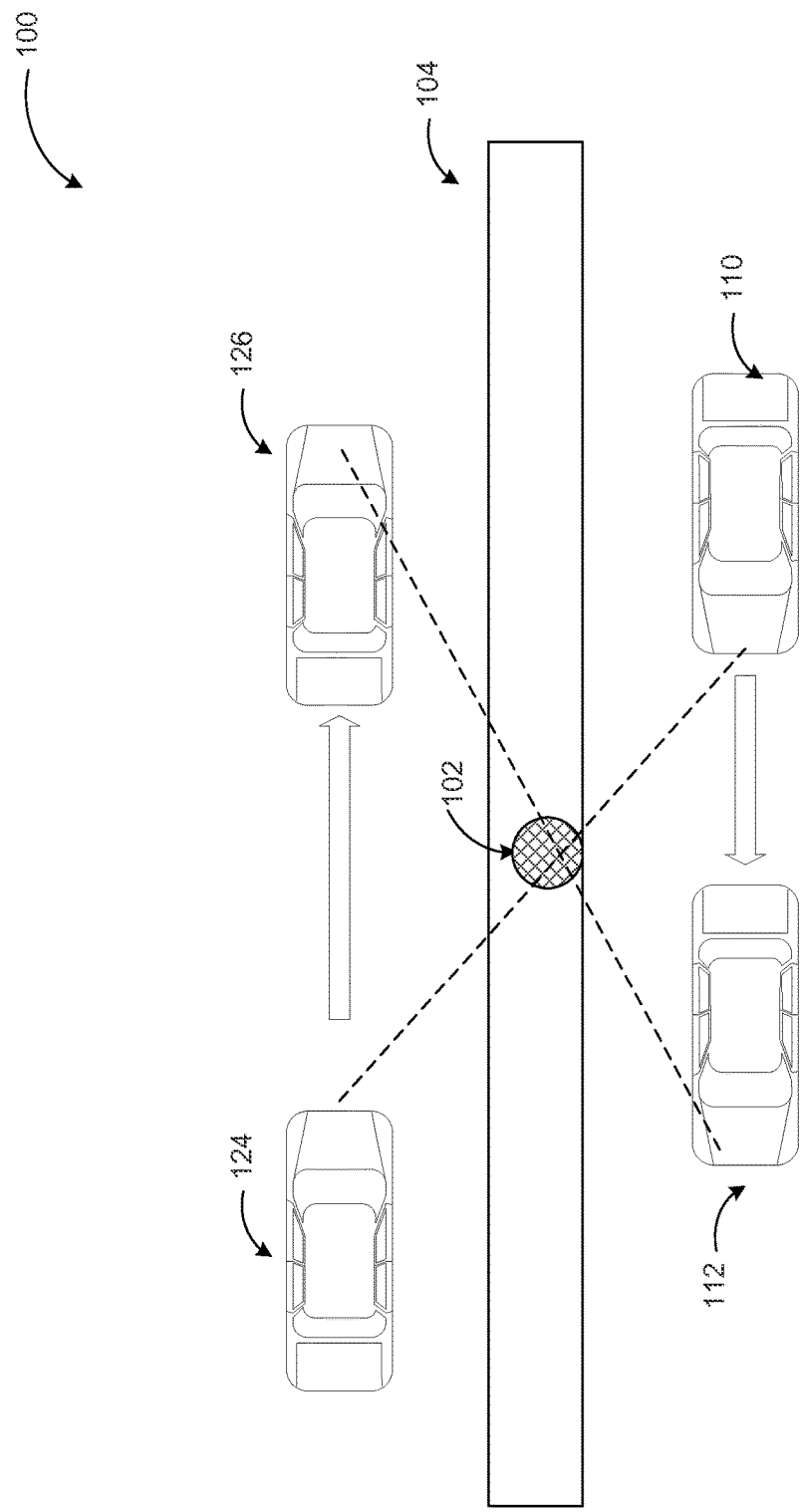
FIG. 1 illustrates an example pair of mobile communication devices passing a target infrastructure to be monitored.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

This disclosure is generally drawn, among other things, to methods, apparatus, systems, devices, and/or computer program products related to roadway infrastructures monitoring based on aggregated mobile vehicle channel parameters.

Briefly stated, technologies are generally described to monitor roadway infrastructure based on aggregated mobile vehicle communication parameters. In some examples, a pair of vehicles with mobile communication devices passing an infrastructure, such as a bridge, may be identified, and the mobile communication devices may exchange a signal during a mobile communication as the vehicles pass the target infrastructure. During the signal exchange, channel characterization data for the target infrastructure may be collected. The channel characterization data may represent propagation conditions of signal waves through the target infrastructure. The channel characterization data may be received at a mobile communication network, where a tomographic model of the target infrastructure may be generated based on extraction and analysis of the channel characterization data. Physical and structural characteristics of the target infrastructure may be determined based on the generated tomographic image of the target infrastructure to facilitate monitoring for degradation and flaws in the target infrastructures.

FIG. 1 illustrates an example pair of mobile communication devices passing a target infrastructure to be monitored, arranged in accordance with at least some embodiments described herein.

As depicted, a diagram 100 illustrates an example target infrastructure 104 to be monitored for structural integrity, defects, and flaws employing a system according to embodiments. Two or more pairs of vehicles (for example, a first vehicle moving from a first position 124 to a second position 126 paired with a second vehicle moving from a first position 110 to a second position 112) may pass the target infrastructure 104 at a given time. As the pairs of vehicles pass the target infrastructure 104, the pairs of vehicles may communicate with each other by exchanging a signal during a communication via a mobile communication device integrated with each of the vehicles. Structural information about a portion 102 of the target infrastructure 104 may be determined based on information and data gathered during the communication and exchanged signal employing radio tomographic imaging. The structural information may be determined by one or more computing devices receiving the exchanged signal information, where the computing devices (more specifically application(s) executed on those computing devices) may analyze information about the exchanged signals to obtain the structural information.

Roadway infrastructures may need to be monitored to detect internal structural flaws, such as material loss, spalling, pop-outs, cracks, honeycombing, corrosion, rusting, and misalignment of bearings and reinforcement structures. Some example roadway structures may include a bridge, a pillar, a tunnel, an overpass, a concrete structure, and a steel reinforced structure. Manual inspection of the roadway infrastructures, such as the target infrastructure 104 illustrated in the diagram 100, may be costly and time consuming due to necessity of an in-person inspection of each of the many infrastructures that make up a roadway system.

Radio tomographic imaging is a technology employed to locate and image objects in areas of interest surrounded by simple and inexpensive radios through the exchange of signals. As the signals are exchanged between at least two radios, objects and structures within the area may reflect and/or absorb the signal, preventing some of the power from reaching its destination. An image of where the power is being absorbed can be formed using channel characterizations (for example, power loss measurements), allowing imaging of the objects within the area. Example embodiments may leverage radio tomographic imaging technology for generation of valuable infrastructure data to efficiently monitor roadway infrastructures at reduced costs.

A system according to embodiments may enable passive monitoring of roadway infrastructures, such as the target infrastructure 104, employing a multitude of mobile communication devices that pass the target infrastructure on a continuous basis over time. An example system may enable a mobile communication device network associated with the multitude of mobile communication devices to coordinate vehicle-to-vehicle communications as a pair of vehicles (for example, the first vehicle moving from the first position 124 to the second position 126 paired with the second vehicle moving from the first position 110 to the second position 112) including mobile communication devices pass the target infrastructure 104 at a given time.

In an example scenario, when the first and second vehicles pass the target infrastructure 104 in opposing paths, the communication devices integrated with the vehicles may exchange a signal, such as a radio frequency signal. The signal may be exchanged through the portion 102 of the target infrastructure 104 when the first vehicle is at the first position 123 and the second vehicle is at the first position 110. A subsequent signal may be exchanged through the portion 102 of the target infrastructure 104 when the first and second vehicles travel to subsequent positions, for example, the second position 126 and the second position 112, respectively. Structural information about the portion 102 of the target infrastructure 104 may be determined based on information and data gathered during each of the exchanged signals between the first and second vehicles. The mobile communication devices may communicate with each other to exchange the signal through an established audio, a video, a data exchange communication, or another mobile wireless communication between the pair of mobile communication devices. The pair of mobile devices may also exchange a signal without an established audio, video, or data exchange communication.

The mobile communication network may gather channel characterization information from the exchanged signal to enable radio tomographic imaging to be applied to provide structural imaging of the portion of the target infrastructure 104. The radio tomographic imaging of the target infrastructure may provide a detailed three-dimensional (3D) image of a structure of the target infrastructure 104, and may provide a detailed view of internal flaws of the target infrastructure 104. As multiple pairs of vehicles pass the target infrastructure 104 over time, large amounts of data from different angles and perspectives may be gathered and aggregated at the mobile communication network to build a detailed model of the target infrastructure 104 and its interior structure to enable thorough structural monitoring.

In an example embodiment, mobile communication devices integrated with vehicles may communicate over a mobile communication network. An example mobile communication network may be an Evolved Universal Mobile Telecommunications System Terrestrial Radio Access Network (eUTRAN), a long term evolution (LTE) network, an LTE-Advanced network, a high speed packet access (HSPA) network, an advanced HSPA network, or other wireless network. Wireless communication between the mobile communication devices over the mobile communication network may be facilitated through multipath or multiple-input and multiple-output (MIMO) wireless communication, which may be based on channel characterization. Channel characterization may include extraction of parameters that represent propagation conditions of radio waves between the sender and receiver communication devices. Channel characterization output parameters may include effects of multipath, spatial distribution, and conductivity of objects between communication devices, and analysis of the output parameters may reveal structural characteristics of the objects between the communication devices.

In a system according to embodiments, wireless communication between mobile communication devices integrated with the pairs of vehicles may be used to continuously evaluate the target infrastructure 104 by gathering channel characterization information and location information during the exchanged communication. The gathered channel characterization information may be aggregated into density and conductance maps of the target infrastructure 104, which may enable evaluation of structural issues of the target infrastructure 104. In a further example embodiment, a number of techniques may be available to convert channel information exchanged during a communication into physical or structural qualities that represent the channel. Example techniques may include, but are not limited to, a stochastic approach, a state space approach, and a scattering approach to convert the gathered channel characterization information into a tomography model of the target infrastructure 104. A sparse sensing approach may allow a high resolution of structural channel data to be extracted from the data exchanged during the communication between the pair of mobile communication devices, which practically involved multiple data exchanges.

Figure 2:
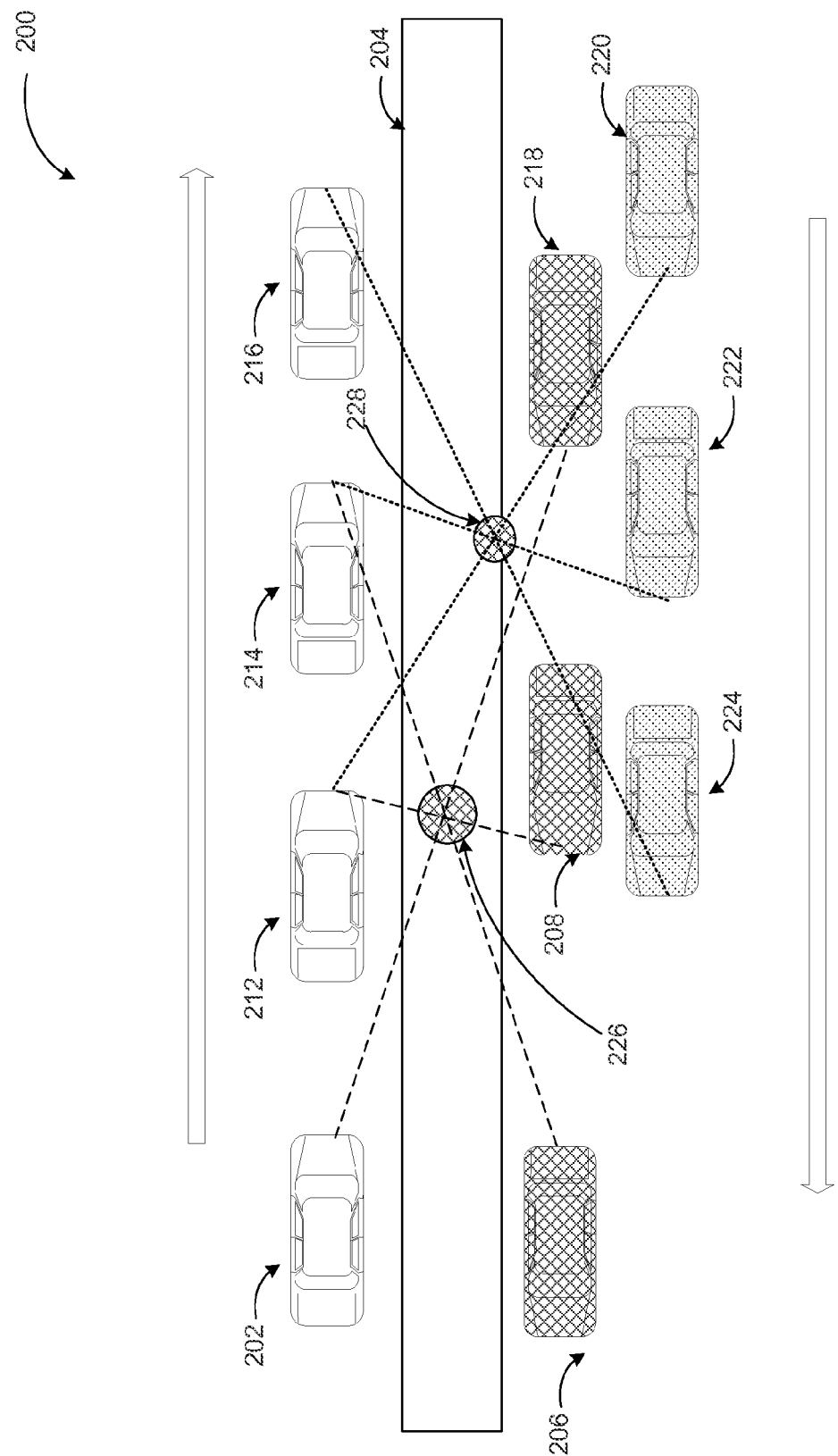
FIG. 2 illustrates an example of multiple pairs of mobile communication devices passing a target infrastructure to be monitored.

FIG. 2 illustrates an example of multiple pairs of mobile communication devices passing a target infrastructure to be monitored, arranged in accordance with at least some embodiments described herein.

As depicted, a diagram 200 illustrates an example target infrastructure 204 to be monitored for structural integrity and flaws employing a system according to embodiments. Two or more pairs of vehicles (for example, vehicles 202 and 218, vehicles 212 and 208, and vehicles 216 and 224) may pass the target infrastructure 204 at a given time. As the pairs of vehicles pass the target infrastructure 204, the pairs of vehicles may communicate with each other by exchanging a signal during a communication. Structural information about one or more portions (for example, a first portion 226 and a second portion 228) of the target infrastructure 204 may be determined based on channel information data gathered during the communication employing radio tomographic imaging.

In a system according to embodiments, mobile communication devices may be integrated with moving vehicles, such as a car, a boat, a train, or other mobile vehicle. As the vehicles, including the mobile communication devices, pass the target infrastructure 204, the mobile communication devices may communicate with each other to exchange a signal. During the signal exchange, channel characterization information about the first portion 226 and the second portion 228 of the target infrastructure may be gathered, for example, by an RF tomographic data builder as part of a structural information infrastructure as discussed below in conjunction with FIG. 3. The channel characterization information may be gathered, and communication parameters may be extracted from the channel characterization information at a mobile communication network associated with the mobile communication devices. The communication parameters may represent the propagation conditions of radio waves through the target infrastructure 204. Based on the extracted communication parameters, a tomography model of the target infrastructure 204 may be generated to model a structure of the target infrastructure to enable analysis of an interior structure of the target infrastructure 204.

In a system according to embodiments, a server or controller (not shown) of the mobile communication network may monitor multiple sets of exchanged signals and collect channel characterization information from the exchanged signals between multiple pairs of mobile communication devices in order to generate detailed images of the target infrastructure. As more sets of data are collected over time from multiple pairs of mobile communication devices, a more detailed and complete image of the target infrastructure 204 may be generated to enable a thorough analysis of an interior structure of the target infrastructure 204.

For example, as illustrated in the diagram 200, as a first vehicle 202 travels from left to right from a first position to new positions (for example, a second position 212, a third position 214 and a fourth position 216) near the target infrastructure 204, a second vehicle 218 may travel from right to left from a first position to new positions (for example, a second position 208 and a third position 206) concurrently. While the first vehicle 202 and the second vehicle 218 pass the target infrastructure 204, the first vehicle 202 and the second vehicle 218 may communicate and exchange signals across the target infrastructure 204. During a first communication or signal exchange when the first vehicle 202 and the second vehicle 218 are in the first positions, channel characterization information about the first portion 226 of the target infrastructure 204 may be exchanged. At new positions of the first vehicle 202 and the second vehicle 218 (for example, the second position 212 of the first vehicle 202 and the second position 208 of the second vehicle 218), channel characterization information about the first portion 226 of the target infrastructure 204 from a different angle may be exchanged.

Similarly a third vehicle 220 may also travel from right to left to new positions (for example, a second position 222 and a third position 224) while the first vehicle 202 travels from left to right. When the first vehicle 202 and the third vehicle 220 pass the target infrastructure, for example, when the first vehicle 202 is at the second position 212 and the third vehicle 220 is in a first position, the first vehicle 202 and the third vehicle 220 may exchange a signal and channel characterization about a second portion 228 of the target infrastructure 204. As the first vehicle 202 and the third vehicle 220 travel to new positions (for example, the third position 214 and the fourth position 216 of the first vehicle and the second position 222 and the third position 224 of the third vehicle 220), additional channel characterization about the second portion 228 of the target infrastructure from different angles may be exchanged.

In a system according to embodiments, different locations, dynamics, and velocities of the vehicles passing the target infrastructure may enable each vehicle pair to generate multiple sample angles through the target infrastructure. Each pair of vehicles may produce a series of sample lines through a portion of the target infrastructure where the two vehicles pass each other, which may provide multiple channel characterization data samples through the portion of the target infrastructure 204. For example, assuming an LTE mobile communication device with a pilot tone of approximately 1,000 times per second, for each vehicle in a vehicle pair traveling at approximately 55 miles per hour, and a data gathering transmission range of about 20 meters, each vehicle pair may generate approximately 500 data angle views as they pass the target infrastructure.

Additionally, multiple vehicles per hour may pass many target infrastructure points of interest, and each pair of vehicles may have different transmitter heights and angles with respect to each other, which may enable a wide range of data samples of portions of the target infrastructure to be gathered. In another example, a vehicle passing over an overpass may pair with another vehicle passing under the overpass, and channel characterization information data about the overpass may be exchanged along a length of the overpass where the vehicles pass.

In a system according to embodiments, the channel characterization information data gathered during the signal exchange between pairs of mobile communication devices integrated with vehicles may be transmitted to the mobile communication network associated with the mobile communication devices. Additionally, the mobile communication devices may also transmit location data to the mobile communication network to enable the location of the target infrastructure 204 to be identified.

Figure 3:
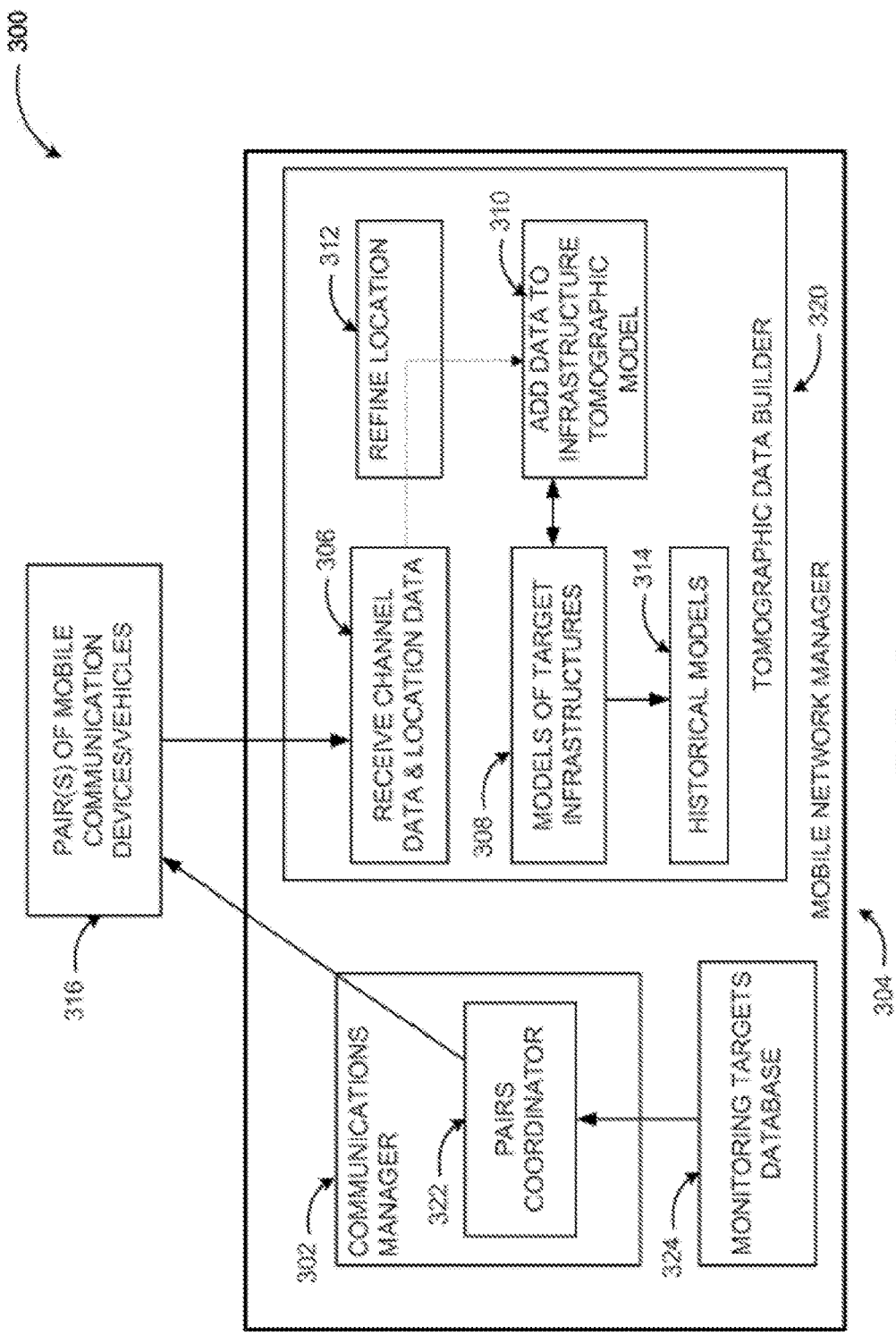
FIG. 3 illustrates an example schematic to monitor roadway infrastructure based on aggregated mobile vehicle communication parameters.

FIG. 3 illustrates an example schematic to monitor roadway infrastructure based on aggregated mobile vehicle communication parameters, arranged in accordance with at least some embodiments described herein.

As depicted, a diagram 300 demonstrates a system configured to collect data about a target infrastructure and building a tomography model to image the target infrastructure for structural monitoring, according to some embodiments. The system may include a mobile network manager 304, a database 324 for monitoring targets, a communications manager 302 including a pairs coordinator 322, a tomographic data builder 320, and pair(s) of mobile communication devices 316. The tomographic data builder 320 component may be configured to perform several operations. For example, at an operation 306 "RECEIVE CHANNEL DATA AND LOCATION DATA", the tomographic data builder 320 may receive channel data and location data from pairs of mobile communication devices. At an operation 312 "REFINE LOCATION OF RECEIVED DATA", the tomographic data builder 320 may refine a location of the received data, for example, using GPS or similar location services information or using known locations of features observed within the samples. At an operation 310 "ADD DATA TO INFRASTRUCTURE TOMOGRAPHIC MODEL", the tomographic data builder 320 may add data to a tomographic model such as metadata associated with the monitored structure. Next, the tomographic data builder may generate the tomographic models 308, and save generated tomographic models to a database of historical models 314.

In a system according to embodiments, the mobile network manager 304 may be configured to identify pairs of mobile communication devices integrated with vehicles passing a target infrastructure and command the pair(s) of mobile communication devices to communicate with each other to gather and save channel characterization data and location data. The mobile network manager 304 may also receive the gathered data and map the data along with received location data, and may aggregate multiple data samples over time. The aggregated data samples may be sorted and analyzed to build a detailed tomography model of the target infrastructure. The mobile network manager 304 may be a mobile network or mobile data carrier that provides mobile interconnectivity for mobile communication devices. The mobile network manager 304 may also be a specialized service associated with mobile communication devices, such as a OPS system, a traffic update system, or other network configured to communicate with and manage mobile communication devices.

In an example embodiment, the database 324 of monitoring targets may store a list of target infrastructures to be monitored. The list of target infrastructures may be provided by a municipality or other agency or source, for example, and may be three-dimensional (3D) points or two-dimensional (2D) map points that represent volume pixels (voxels) that a client would like to be monitored by the mobile network manager. The communications manager 302 may be in contact with multiple mobile communication devices associated with the mobile network manager 304. The communications manager 302 may consult the database 324 of monitoring targets to identify a target infrastructure that two or more vehicles may be approaching. The pairs coordinator 322, of the communications manager 302 may compose a tomography pair, or a pair or more of mobile communication devices 316 (integrated with the two or more vehicles) that should communicate while passing the identified target infrastructure. The communications manager 302 may instruct the pair of mobile communication devices 316 to communicate with each other through communication signals as the pair of mobile communication devices pass the target infrastructure. The communications manager 302 may also instruct at least one of the pair of mobile communication devices 316 to collect information about the signals including channel characterization data.

In an example embodiment, the tomographic data builder 320 may receive the collected channel characterization data. Additionally, location data from the mobile communication devices may also be received at the tomographic data builder. Location data may be transmitted by each pair of the mobile communication devices 316. The location data may include location data determined from a UPS, an accelerometer, or other location sensing application integrated with the mobile communication devices 316. For example, vehicles that use autonomy systems, such as automatic help with lane centering, may have fine resolution location data, and may employ a localization algorithm to estimate a vehicle state, where the state may include a position, altitude, and velocity. The tomographic data builder 320 may further refine the location of the received data at the operation 312 by performing sliding window matches to better align existing data with newly received data, using detected features like endpoints, supports, or signs to reference data and refine precise locations.

After a location of the received data has been determined and refined, the data may be added to the tomographic models 310 to generate a thorough tomographic model of the target infrastructure. The tomographic model of the target infrastructure may be generated by extracting parameters from the channel characterization data that represent propagation conditions of radio waves between the mobile communication devices through the target infrastructure. Channel characterization output parameters may include effects of multipath, spatial distribution, dielectric performance, and conductivity of objects between communication devices. Some example communication parameters may include an amplitude, a frequency, or a phase of the radio waves as they pass through the target infrastructure.

The newly received data may be added to the tomographic model to continuously improve and refine the tomographic model of the target infrastructure. Furthermore, data may be received at the mobile network manager 304 from multiple pairs of mobile communication devices that pass the target infrastructure over a period of time. The data from the multiple pairs of mobile communication devices may be aggregated to continuously build and improve the tomographic model as more data is received over time.

The updated tomographic model of the target infrastructure may be stored in the database of historical models 314 as a function of a date and a time to enable a structure of the target infrastructure to be analyzed and monitored at various time periods. Analysis of the tomographic models of a particular target infrastructure over time may enable changes in a structure to be detected, which may enable accurate analysis of degradation or corrosion of a particular structure over time. The database of historical models 314 may be provided to clients who specify the monitoring targets, such as municipalities, monitoring agencies, insurance companies, and other similar clients. The tomographic models may be employed by the requesting clients to detect target infrastructure flaws including material loss, spalling, pop-outs, cracks, honeycombing, corrosion, rusting, and misalignment of bearings and reinforcement structures, as some examples.

Figure 4:
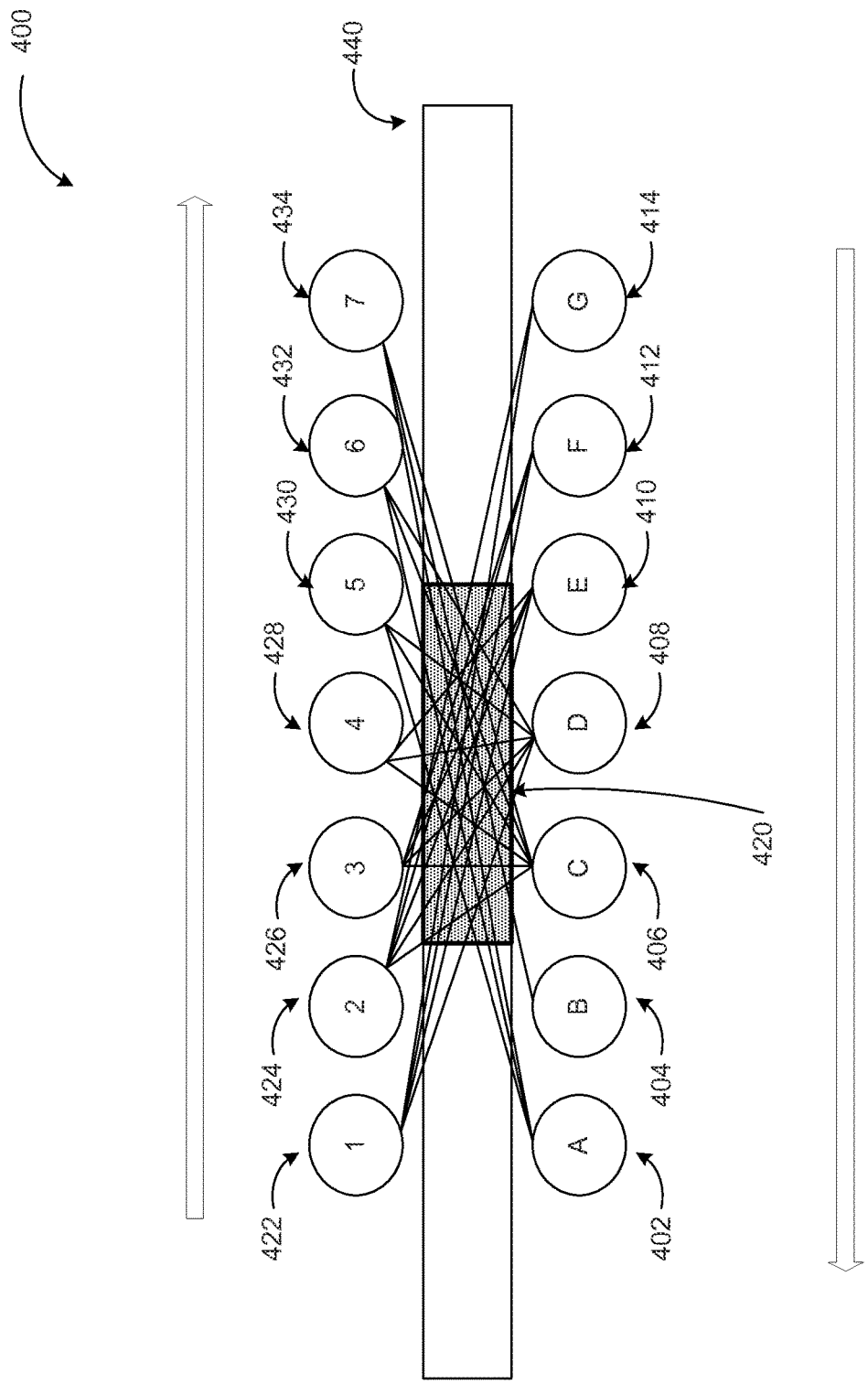
FIG. 4 illustrates example tomography data points gathered from multiple pairs of communication devices passing a target infrastructure.

FIG. 4 illustrates example tomography data points gathered from multiple pairs of communication devices passing a target infrastructure, arranged in accordance with at least some embodiments described herein.

As depicted, a diagram 400 illustrates multiple potential mobile communication device pairings and a target portion 420 of an infrastructure 440 to be monitored. In the diagram 400, points 422-434 and points 402-414 may represent one or more vehicles passing the infrastructure 440 at various times. Each vehicle may include a mobile communication device configured to exchange a signal with other mobile communication devices over a mobile communication network.

As discussed in conjunction with FIG. 3, the mobile communication network associated with mobile communication devices may employ a pairs coordinator to identify pairs of mobile communication devices passing the infrastructure 440 to collect infrastructure data. The pairs coordinator may apply a matching technique and algorithm to determine a timing and position of pairs of mobile communication devices to select an appropriate pair of mobile communication devices for collecting desired data. Each vehicle may have a variable velocity and position, and there may likely be a delay between instructions sent to the mobile communication devices to collect a signal, and an establishment of a connection to exchange the signal and collect requested data. The pairs coordinator may use location and velocity information of each vehicle to predictively allow for an expected distance of travel during the delay to target a pair of mobile communication devices passing a particular point at a given time.

In an example scenario, a first target pair for a particular monitoring target may be target point 3-E (corresponding to the points 426 and 410 respectively). The pairs coordinator may gather data on vehicles passing by and may compute a velocity (v) times setup time (t) as a delay or a displacement offset (D) for each vehicle. For example, v1×t1=D1 for a first vehicle, and v2×t2=D2 for a second vehicle. Based on the calculated displacement offsets D1 and D2, the pairs coordinator may deliver measurement instructions to one or more pairs of vehicles anticipated to pass through the desired target point 3-E. The pairs coordinator may instruct each mobile communication device associated with each vehicle to start a communication a minimum of the displacement offset in advance, but not so far in advance that initial communications will be over and replaced by beacon exchanges. Once at least one data for a target point has been collected, the data may be added to the tomographic model for the target infrastructure, and a sparse sensing algorithm may be used to evaluate which additional target points are needed to build a complete tomographic model. The result may be a reduced list of potential target points to select from, as the sparse sensing algorithm may not need all the tomographic pairs to be fulfilled. The pairs coordinator may employ a similar process to identify additional pairs of mobile communication devices passing through the remaining list of potential target points.

While the above process for selecting a target point of a target infrastructure and potential pair of mobile communication devices passing the selected target point is described in terms of a single or few target points, the process may be applied to multiple thousands of potential target points, and may reduce to a few actual data pairs after data is gathered and sparse sensing is applied. The sparse sensing algorithm may enable pairing between a small number of mobile communication devices to provide rich data for target points of a target infrastructure.

Figure 5:
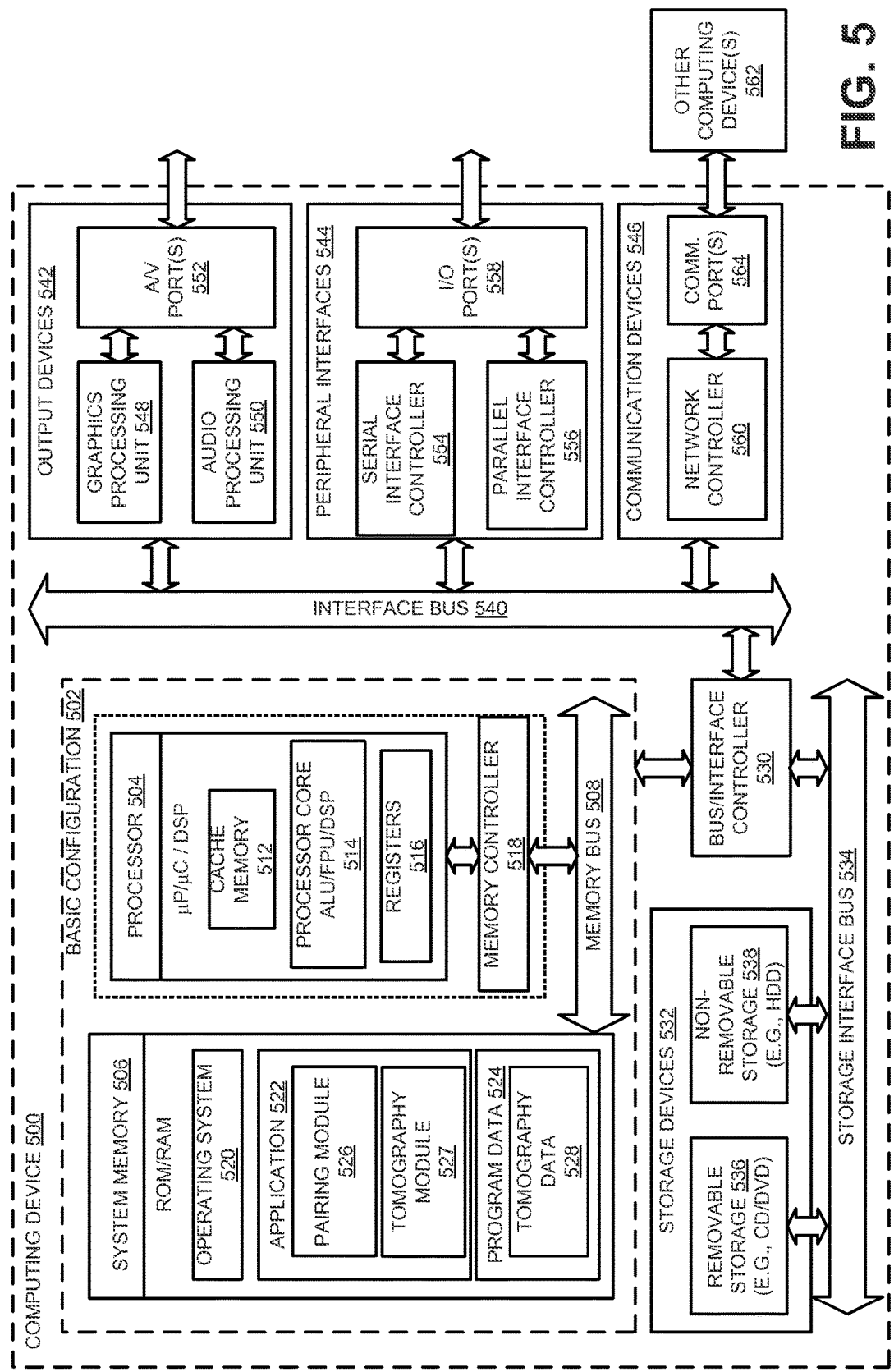
FIG. 5 illustrates a general purpose computing device, which may be used to aggregate mobile vehicle communication parameters to monitor roadway infrastructure.

FIG. 5 illustrates a general purpose computing device, which may be used to aggregate mobile vehicle communication parameters to monitor roadway infrastructure, arranged in accordance with at least some embodiments described herein.

For example, a computing device 500 may be used as a server, desktop computer, portable computer, smart phone, special purpose computer, or similar device. In an example basic configuration 502, the computing device 500 may include one or more processors 504 and a system memory 506. A memory bus 508 may be used for communicating between the processor 504 and the system memory 506. The basic configuration 502 is illustrated in FIG. 4 by those components within the inner dashed line.

Depending on the desired configuration, the processor 504 may be of any type, including but not limited to a microprocessor (μP), a microcontroller (μC), a digital signal processor (DSP), or any combination thereof. The processor 504 may include one or more levels of caching, such as a cache memory 512, one or more processor cores 514, and registers 516. The example processor cores 514 may (each) include an arithmetic logic unit (ALU), a floating point unit (FPU), a digital signal processing core (DSP core), or any combination thereof. An example memory controller 518 may also be used with the processor 504, or in some implementations, the memory controller 518 may be an internal part of the processor 504.

Depending on the desired configuration, the system memory 506 may be of any type including but not limited to volatile memory (such as RAM), non-volatile memory (such as ROM, flash memory, etc.) or any combination thereof. The system memory 506 may include an operating system 520, one or more applications 522, and program data 524. The application 522 may include a pairing module 526 and a tomography module 527, which may be an integral part of the application 522 or a separate application on its own.

The pairing module 526 may facilitate identifying a pair of mobile communication devices approaching a target infrastructure, and may coordinate a signal exchange between the pair of mobile communication devices as the mobile communication devices pass the target infrastructure. The tomography module 527 may facilitate aggregating information about the exchanged signals from the mobile communication devices and analyzing the aggregated information about the signals to extract channel data to build a tomography model of the target infrastructure in order to determine structural characteristics of the target infrastructure. The program data 524 may include, among other data, tomography data 528 for the target infrastructure that represents structural characteristics of the target infrastructure, for example, as described herein.

The computing device 500 may have additional features or functionality, and additional interfaces to facilitate communications between the basic configuration 502 and any desired devices and interfaces. For example, a bus/interface controller 530 may be used to facilitate communications between the basic configuration 502 and one or more data storage devices 532 via a storage interface bus 534. The data storage devices 532 may be one or more removable storage devices 536, one or more non-removable storage devices 538, or a combination thereof. Examples of the removable storage and the non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

The system memory 506, the removable storage devices 536 and the non-removable storage devices 538 are examples of computer storage media. Computer storage media includes, but is not limited to, RAM, ROM, EEPROM, flash memory or other memory technology, CD-ROM, digital versatile disks (DVDs), solid state drives (SSDs), or other optical storage, magnetic cassettes, magnetic tape, magnetic disk storage or other magnetic storage devices, or any other medium which may be used to store the desired information and which may be accessed by the computing device 500. Any such computer storage media may be part of the computing device 500.

The computing device 500 may also include an interface bus 540 for facilitating communication from various interface devices (for example, one or more output devices 542, one or more peripheral interfaces 544, and one or more communication devices 546) to the basic configuration 502 via the bus/interface controller 530. Some of the example output devices 542 include a graphics processing unit 548 and an audio processing unit 550, which may be configured to communicate to various external devices such as a display or speakers via one or more A/V ports 552. One or more example peripheral interfaces 544 may include a serial interface controller 554 or a parallel interface controller 556, which may be configured to communicate with external devices such as input devices (for example, keyboard, mouse, pen, voice input device, touch input device, etc.) or other peripheral devices (for example, printer, scanner, etc.) via one or more I/O ports 558. An example communication device 546 includes a network controller 560, which may be arranged to facilitate communications with one or more other computing devices over a network communication link via one or more communication ports 564. The one or more other computing devices 562 may include servers, client devices, smart appliances, and comparable devices.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 500 may be implemented as a part of a general purpose or specialized server, mainframe, or similar computer that includes any of the above functions. The computing device 500 may also be implemented as a personal computer including both laptop computer and non-laptop computer configurations.

Example embodiments may also include methods to aggregate mobile vehicle communication parameters to monitor roadway infrastructure. These methods can be implemented in any number of ways, including the structures described herein. One such way may be by machine operations, of devices of the type described in the present disclosure. Another optional way may be for one or more of the individual operations of the methods to be performed in conjunction with one or more human operators performing some of the operations while other operations may be performed by machines. These human operators need not be collocated with each other, but each can be only with a machine that performs a portion of the program. In other embodiments, the human interaction can be automated such as by pre-selected criteria that may be machine automated.

Figure 6:
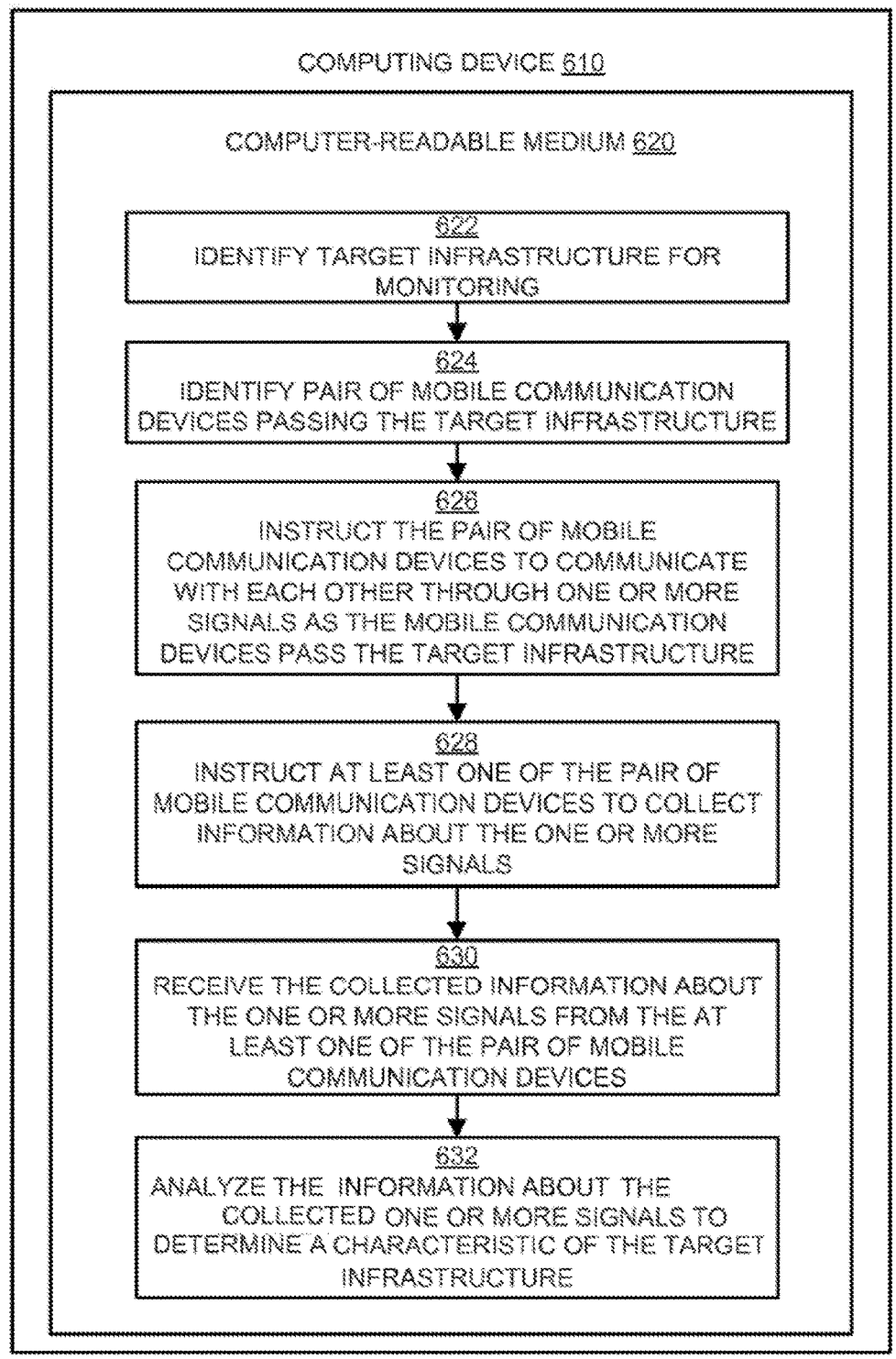
FIG. 6 is a flow diagram illustrating an example method to aggregate mobile vehicle communication parameters to monitor roadway infrastructure that may be performed by a computing device such as the computing device in FIG. 5.

FIG. 6 is a flow diagram illustrating an example method to aggregate mobile vehicle communication parameters to monitor roadway infrastructure that may be performed by a computing device such as the computing device in FIG. 5, arranged in accordance with at least some embodiments described herein.

Example methods may include one or more operations, functions or actions as illustrated by one or more of blocks 622, 624, 626, 628, 630, and 632. The operations described in the blocks 622 through 632 may also be stored as computer-executable instructions in a computer-readable medium such as a computer-readable medium 620 of a computing device 610.

An example process to aggregate mobile vehicle communication parameters to monitor roadway infrastructure may begin with block 622, "IDENTIFY TARGET INFRASTRUCTURE FOR MONITORING," where a target infrastructure (for example, the target infrastructure 104) such as a bridge, a pillar, a tunnel, an overpass, a concrete structure, or a steel reinforced structure may be identified to monitor structural characteristics of the target infrastructure. The target infrastructure may be selected from a database of infrastructures.

Block 622 may be followed by block 624, "IDENTIFY PAIR OF MOBILE COMMUNICATION DEVICES PASSING THE TARGET INFRASTRUCTURE," where two mobile communication devices approaching the target infrastructure at different angles may be identified. The mobile communication devices may be channel sensing devices configured to exchange communication signals and to collect channel characterization data during a mobile device communication exchange.

Block 624 may be followed by block 626, "INSTRUCT THE PAIR OF MOBILE COMMUNICATION DEVICES TO COMMUNICATE WITH EACH OTHER THROUGH ONE OR MORE SIGNALS AS THE MOBILE COMMUNICATION DEVICES PASS THE TARGET INFRASTRUCTURE," where the mobile communication devices may communicate with each other through one or more signals, such as radio frequency communication signals, as the pair of mobile communication devices pass the target infrastructure (for example, the target infrastructure 104). Additionally, the mobile devices may communicate with each other to exchange a signal through one or more of an established audio, a video, or a data exchange communication between the pair of mobile communication devices. The pair of mobile devices may also exchange a signal without an established audio, video, or data exchange communication.

Block 626 may be followed by block 628, "INSTRUCT AT LEAST ONE OF THE PAIR OF MOBILE COMMUNICATION DEVICES TO COLLECT INFORMATION ABOUT THE ONE OR MORE SIGNALS," where at least one of the communication devices may collect information about the signal(s) exchanged between the pair of communication devices.

Block 628 may be followed by block 630, "RECEIVE THE COLLECTED INFORMATION ABOUT THE ONE OR MORE SIGNALS FROM THE AT LEAST ONE OF THE PAIR OF MOBILE COMMUNICATION DEVICES," where the information about the collected signal(s) may be received at a mobile communication network for analysis of the signals to determine structural characteristic data about the target infrastructure. The collected information about the signal data may be received at a tomography builder component (for example, the tomography data builder 320 of FIG. 3) of the network.

Block 630 may be followed by block 632, "ANALYZE THE INFORMATION ABOUT THE COLLECTED ONE OR MORE SIGNALS TO DETERMINE A CHARACTERISTIC OF THE TARGET INFRASTRUCTURE," where the tomography builder component (for example, the tomography data builder 320 of FIG. 3) of the network may analyze the information about the collected signal(s) by assembling a tomographic model of the target infrastructure based on the analyzed one or more signals. The tomography builder component may extract channel state data from the analyzed information from the one or more signals that represent propagation conditions of the one or more signals through the target infrastructure. The channel state data may include effects of a multipath and a spatial distribution an/or a conductivity of the target infrastructure. Additionally, the extracted channel state data may be aggregated into a density and conductance map of the target infrastructure to assemble the tomographic model. Based on the tomographic model, structural characteristics of the target infrastructure may be determined, and flaws of the target infrastructure may be detected. Example flaws may include material loss, spalling, pop-outs, cracks, honeycombing, corrosion, rusting, and misalignment of bearings and/or reinforcement structures.

The blocks included in the above described process are for illustration purposes. Aggregation of mobile vehicle communication parameters to monitor roadway infrastructure may be implemented by similar processes with fewer or additional blocks. In some embodiments, the blocks may be performed in a different order. In some other embodiments, various blocks may be eliminated. In still other embodiments, various blocks may be divided into additional blocks, or combined together into fewer blocks.

Figure 7:
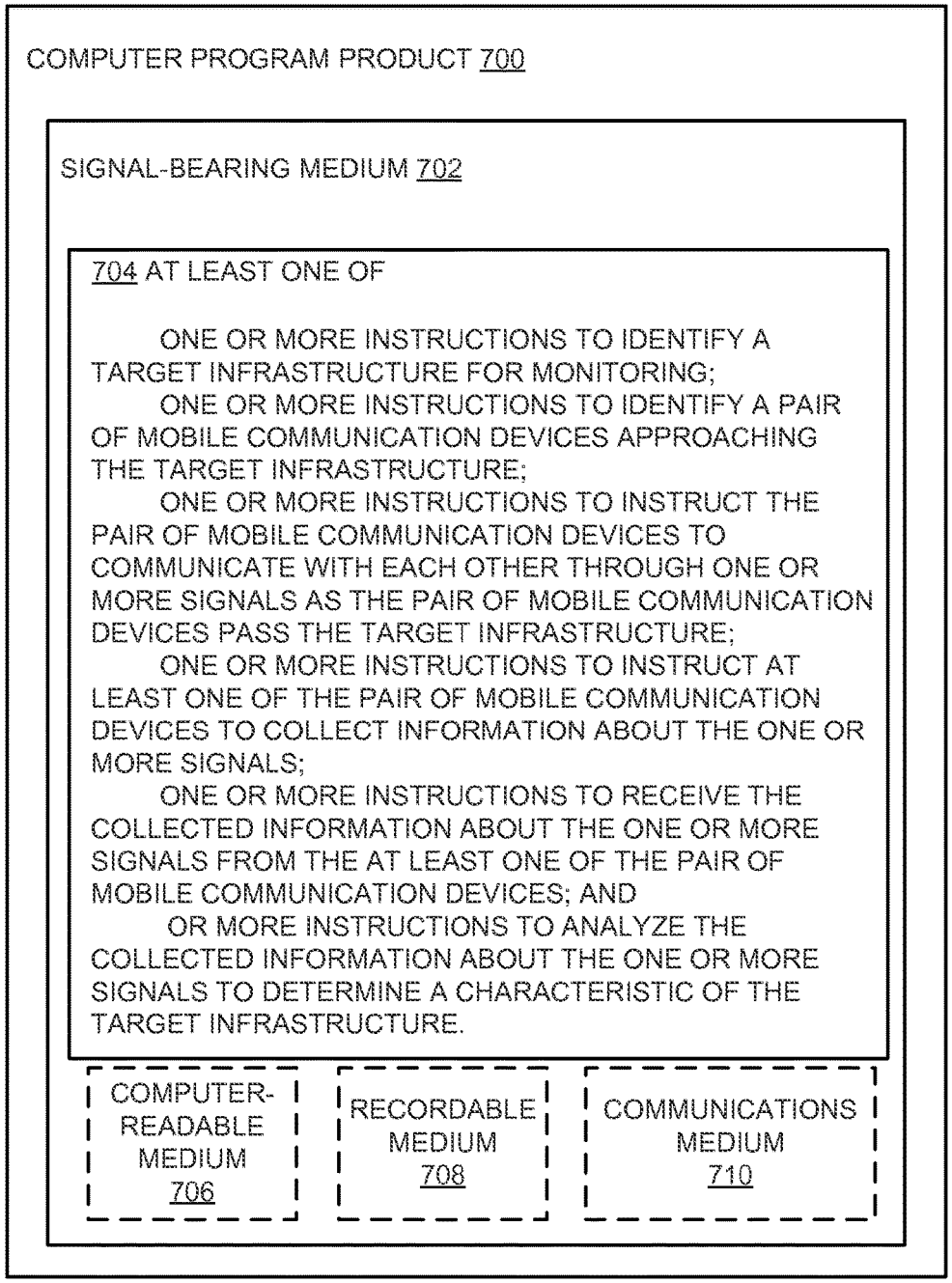
FIG. 7 illustrates a block diagram of an example computer program product, all arranged in accordance with at least some embodiments as described herein.

FIG. 7 illustrates a block diagram of an example computer program product, arranged in accordance with at least some embodiments described herein.

In some embodiments, as shown in FIG. 7, the computer program product 700 may include a signal bearing medium 702 that may also include one or more machine readable instructions 704 that, when executed by, for example, a processor may provide the functionality described above with respect to FIG. 5. Thus, for example, referring to the processor 504 in FIG. 5, the pairing module 526 and/or the tomography module 527 executed on the processor 504 may undertake one or more of the tasks shown in FIG. 7 in response to the instructions 704 conveyed to the processor 504 by the signal bearing medium 702 to perform actions associated with aggregating mobile vehicle communication parameters to monitor roadway infrastructure as described herein. Some of those instructions may include, for example, one or more instructions to identify a target infrastructure for monitoring, identity a pair of mobile communication devices approaching the target infrastructure, instruct the pair of mobile communication devices to communicate with each other through one or more signals as the pair of mobile communication devices pass the target infrastructure, instruct at least one of the pair of mobile communication devices to collect information about the one or more signals, receive the collected information about the one or more signals from the at least one of the pair of mobile communication devices, and analyze the collected information about the one or more signals to determine a characteristic of the target infrastructure, according to some embodiments described herein.

In some implementations, the signal bearing medium 702 depicted in FIG. 7 may encompass a computer-readable medium 706, such as, but not limited to, a hard disk drive (HDD), a solid state drive (SSD), a Compact Disc (CD), a Digital Versatile Disk (DVD), a digital tape, memory, etc. In some implementations, the signal bearing medium 702 may encompass a recordable medium 708, such as, but not limited to, memory, read/write (R/W) CDs, R/W DVDs, etc. In some implementations, the signal bearing medium 702 may encompass a communications medium 710, such as, but not limited to, a digital and/or an analog communication medium (for example, a fiber optic cable, a waveguide, a wired communications link, a wireless communication link, etc.). Thus, for example, the computer program product 700 may be conveyed to one or more modules of the processor 504 of FIG. 5 by an RF signal bearing medium, where the signal bearing medium 702 may be conveyed by the wireless communications medium 710 (for example, a wireless communication medium conforming with the IEEE 802.11 standard).

The present disclosure provides a method to monitor roadway infrastructure based on aggregated mobile vehicle communication parameters. The method may include identifying a target infrastructure to monitor, identifying a pair of mobile communication devices approaching the target infrastructure, instructing the pair of mobile communication devices to communicate with each other through one or more signals as the pair of mobile communication devices pass the target infrastructure, instructing at least one of the pair of mobile communication devices to collect information about the one or more signals, receiving the collected information about the one or more signals from the at least one of the pair of mobile communication devices, and analyzing the collected information about the one or more signals to determine a structural characteristic of the target infrastructure.

According to some example methods, instructing the pair of mobile communication devices to communicate with each other may include causing the pair of mobile communication devices to exchange radio frequency communication signals.

According to some example methods, analyzing the information about the collected one or more signals may include determining one or more communication parameters including an amplitude, a frequency, or a phase.

According to some example methods, the mobile communication devices may be integrated with a car, a boat, and/or a train. The target infrastructure may be a bridge, a pillar, a tunnel, an overpass, a concrete structure, and/or a steel reinforced structure.

According to some other examples, the method may also include receiving location data from each of the pair of mobile communication devices. Receiving the location data may include receiving the location data from a GPS and/or an accelerometer integrated with the mobile communication device. The method may also include refining locations of the received one or more signals employing the location data.

According to other example methods, instructing the pair of mobile communication devices to communicate with each other may include causing an audio, a video, or a data exchange communication to be established between the pair of mobile communication devices. According to some examples, instructing the pair of mobile communication devices to communicate with each other includes causing the pair of mobile communication devices to communicate without an audio, a video, or a data exchange communication to be established between the pair of mobile communication devices.

According to some examples, the method may also include aggregating the received information about the one or more signals from multiple pairs of mobile communication devices that pass the target infrastructure over a period of time. Identifying the target infrastructure for monitoring may include identifying the target infrastructure from a database of target infrastructures selected for monitoring.

According to other examples, the method may also include assembling a tomographic model of the target infrastructure based on the analyzed information about the one or more signals. The tomographic model may be a three-dimensional (3D) model. Assembling the tomographic model may include extracting channel state data from the analyzed one or more signals that represent propagation conditions of the one or more signals through the target infrastructure. The channel state data may include effects of: a multipath, a spatial distribution and/or a conductivity of the target infrastructure.

According to some example methods, assembling the tomographic model may include aggregating the extracted channel state data into a density and conductance map of the target infrastructure. Assembling the tomographic model further may also include employing a sparse sensing approach, a stochastic approach, a state space approach, and/or a scattering approach. The method may further include updating the tomographic model with newly received data from one or more pairs of mobile communication devices.

According to further examples, the method may also include storing the tomographic model in a historical database as a function of a date and a time for monitoring the target infrastructure at a particular time. The method may also include employing the tomographic model to detect target infrastructure flaws including material loss, spalling, pop-outs, cracks, honeycombing, corrosion, rusting, and/or misalignment of bearings and reinforcement structures. The method may further include instructing at least one of the mobile communication devices to analyze the collected signals and to provide analysis results to a tomographic data builder to assemble a tomographic model.

According to other examples, the present disclosure describes a controller to monitor roadway infrastructure based on aggregated mobile vehicle communication parameters. The controller may include a memory configured to store instructions, a communication module configured to facilitate communications with one or more mobile communication devices and to instruct the mobile communication devices to exchange one or more signals, and a processor coupled to the memory and the communication module, the processor configured to execute a tomography application in conjunction with the instructions stored in the memory. The tomography application may be configured to identify a target infrastructure for monitoring, identify a pair of mobile communication devices approaching the target infrastructure via a pairing module of the tomography application, control the communication module to instruct pair of mobile communication devices to communicate with each other through the one or more signals as the pair of mobile communication devices pass the target infrastructure, control the communication module to instruct at least one of the pair of mobile communication devices to collect information about the one or more signals, receive the collected information about the one or more signals from the at least one of the pair of mobile communication devices, and analyze the collected information about the one or more signals to determine a structural characteristic of the target infrastructure.

According to some examples, the one or more signals may be radio frequency communication signals and the tomography application may be further configured to analyze an amplitude, a frequency, and/or a phase of the radio frequency communication signals. The mobile communication devices include a citizens band radio, a cellular communication device, a wireless data exchange device, and/or a global positioning device. The mobile communication devices may be integrated with a car, a boat, or a train. The target infrastructure may be a bridge, a pillar, a tunnel, an overpass, a concrete structure, or a steel reinforced structure.

According to some other examples, the tomography application may be configured to instruct the pair of mobile communication devices to communicate with each other by causing an audio, a video, or a data exchange communication to be established between the pair of mobile communication devices. The tomography application may be further configured to aggregate the received one or more signals from multiple pairs of mobile communication devices that pass the target infrastructure over a period of time.

According to other examples, the tomography application may be further configured to assemble a tomographic model of the target infrastructure based on extraction of channel state data from the analyzed one or more signals that represent propagation conditions of the one or more signals through the target infrastructure, wherein the channel state data includes effects of a multipath, a spatial distribution, and/or a conductivity of the target infrastructure between the pair of mobile communication devices, and aggregate the extracted channel state data into a density and conductance map of the target infrastructure.

According to further examples, the tomography application may be further configured to store the tomographic model in a historical database as a function of a date and a time to monitor the target infrastructure at a particular time, and employ the tomographic model to detect target infrastructure flaw. The tomography application may be further configured to provide the tomographic model to a requesting service.

According to other examples, the present disclosure describes a mobile communication network to monitor roadway infrastructure based on aggregated mobile vehicle communication parameters. The mobile communication network may include a plurality of mobile communication devices, and one or more servers to manage communication among the plurality of mobile communication devices, where least one of the one or more servers may be configured to identify a target infrastructure for monitoring, identify pairs of mobile communication devices approaching the target infrastructure, instruct the pairs of mobile communication devices to communicate with each other through the one or more signals as the pairs of mobile communication devices pass the target infrastructure, instruct one or more of the pairs of mobile communication devices to collect information about the one or more signals, receive the collected information about the one or more signals from the one or more of the pairs of mobile communication devices, aggregate the received information about the one or more signals from the pairs of mobile communication devices that pass the target infrastructure over a period of time, and analyze the aggregated information about the one or more signals to determine a structural characteristic of the target infrastructure.

According to some examples, the mobile communication network may be an Evolved Universal Mobile Telecommunications System Terrestrial Radio Access Network (eU-TRAN), a long term evolution (LTE) network, an LTE-Advanced network, a high speed packet access (HSPA) network, or an advanced HSPA network. The one or more signals may be radio frequency communication signals and the at least one of the servers may be further configured to analyze an amplitude, a frequency, and/or a phase of the radio frequency communication signals.

According to other examples, the at least one of the servers may be further configured to receive location data from each of the pairs of mobile communication devices, and refine a location of the received one or more signals employing the location data. At least one other of the one or more servers may be configured to facilitate an audio, a video, or a data exchange communication between the pairs of mobile communication devices. At least one of the servers may be further configured to instruct the one or more of the pairs of mobile communication devices to collect the one or more signals during the facilitated communication.

According to further examples, the at least one of the servers may be further configured to assemble a three-dimensional (3D) tomographic model of the target infrastructure based on the analyzed aggregated signals, update the tomographic model with newly received data from other pairs of mobile communication devices, store the tomographic model in a historical database as a function of a date and a time to monitor the target infrastructure at a particular time, and employ the tomographic model to detect target infrastructure flaw.

According to yet other examples, the present disclosure describes a computer readable storage medium with instructions stored thereon, which when executed on one or more computing devices execute a method to monitor roadway infrastructure based on aggregated mobile vehicle communication parameters.

There are various vehicles by which processes and/or systems and/or other technologies described herein may be effected (for example, hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, may be equivalently implemented in integrated circuits, as one or more computer programs running on one or more computers (for example, as one or more programs running on one or more computer systems), as one or more programs running on one or more processors (for example as one or more programs running on one or more microprocessors), as firmware, or as virtually any combination thereof and that designing the circuitry and/or writing the code for the software and or firmware would be possible in light of this disclosure.

The present disclosure is not to be limited in terms of the particular embodiments described in this application, which are intended as illustrations of various aspects. Many modifications and variations can be made without departing from its spirit and scope Functionally equivalent methods and apparatuses within the scope of the disclosure, in addition to those enumerated herein, will be possible from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, systems, or components, which can, of course, vary. It is also to be understood that the terminology used herein is for the purpose of describing particular embodiments only, and is not intended to be limiting.

In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive (HDD), a Compact Disc (CD), a Digital Versatile Disk (DVD), a digital tape, a computer memory, etc.; and a transmission type medium such as a digital and/or an analog communication medium (for example, a fiber optic cable, a waveguide, a wired communication link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops.

A typical data processing system may be implemented utilizing any suitable commercially available components, such as those typically found in data computing/communication and/or network computing/communication systems. The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that particular functionality is achieved. Hence, any two components herein combined to achieve a particular functionality may be seen as "associated with" each other such that the particular functionality is achieved, irrespective of architectures or intermediate components. Likewise, any two components so associated may also be viewed as being "operably connected", or "operably coupled", to each other to achieve the particular functionality, and any two components capable of being so associated may also be viewed as being "operably couplable", to each other to achieve the particular functionality. Specific examples of operably couplable include but are not limited to physically connectable and/or physically interacting components and/or wirelessly interactable and/or wirelessly interacting components and/or logically interacting and/or interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

The terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations).

Furthermore, in those instances where a convention analogous to "at least one of A, B, and C, etc." is used, in general, such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method to monitor roadway infrastructure based on aggregated mobile vehicle communication parameters, the method comprising:
   identifying a target infrastructure to monitor;
   identifying a pair of mobile communication devices that approach the target infrastructure;
   instructing the pair of mobile communication devices to communicate with each other through one or more signals as the pair of mobile communication devices pass the target infrastructure;
   instructing at least one mobile communication device of the pair of mobile communication devices to collect information about the one or more signals;
   receiving the collected information about the one or more signals from the at least one mobile communication device of the pair of mobile communication devices;
   analyzing the collected information about the one or more signals to determine a structural characteristic of the target infrastructure;
   instructing a result of the analysis to be provided to a tomographic data builder, wherein the provided result of the analysis is usable to assemble a tomographic model; and
   assembling the tomographic model of the target infrastructure based on the analyzed information about the one or more signals, wherein assembling the tomographic model comprises extracting, from the analyzed information about the one or more signals, channel state data that represent propagation conditions of the one or more signals through the target infrastructure.

2. The method according to claim 1, wherein instructing the pair of mobile communication devices to communicate with each other comprises causing the pair of mobile communication devices to exchange radio frequency communication signals.

3. The method according to claim 1, wherein analyzing the collected information about the one or more signals comprises determining one or more communication parameters that includes one of: an amplitude, a frequency, or a phase of the one or more signals.

4. The method according to claim 1, wherein identifying the target infrastructure to monitor comprises identifying the target infrastructure from a database of target infrastructures selected to be monitored.

5. The method according to claim 1, wherein extracting the channel state data from the analyzed information about the one or more signals includes extracting data indicative of effects of one or more of: a multipath, a spatial distribution, and a conductivity of the target infrastructure.

6. The method according to claim 1, wherein assembling the tomographic model of the target infrastructure comprises aggregating the extracted channel state data into a density and conductance map of the target infrastructure.

7. The method according to claim 1, wherein assembling the tomographic model of the target infrastructure comprises employing one or more of: a sparse sensing approach, a stochastic approach, a state space approach, and a scattering approach.

8. The method according to claim 1, further comprising:
   updating the tomographic model with newly received data from additional one or more pairs of mobile communication devices.

9. The method according to claim 1, further comprising:
   storing the tomographic model in a historical database as a function of a date and a time to monitor the target infrastructure at a particular time.

10. The method according to claim 1, further comprising:
    employing the tomographic model to detect target infrastructure flaws that include one or more of: material loss, spalling, pop-outs, cracks, honeycombing, corrosion, rusting, and misalignment of bearings and reinforcement structures.

11. A system to monitor roadway infrastructure based on aggregated mobile vehicle communication parameters, the system comprising:
    a memory configured to store instructions;
    a processor coupled to the memory, wherein the processor is configured to execute the instructions stored in the memory to perform or control performance of operations to:
      identify a target infrastructure to monitor;
      identify a pair of mobile communication devices that approach the target infrastructure;
      instruct the pair of mobile communication devices to communicate with each other through one or more signals as the pair of mobile communication devices pass the target infrastructure;
      instruct at least one mobile communication device of the pair of mobile communication devices to collect information about the one or more signals;
      obtain the collected information about the one or more signals from the at least one mobile communication device of the pair of mobile communication devices;
      analyze the collected information about the one or more signals to determine a structural characteristic of the target infrastructure; and
      instruct a result of the analysis to be provided to a tomographic data builder, wherein the provided result of the analysis is usable to assemble a tomographic model.

12. The system according to claim 11, wherein the processor is further configured to execute the instructions stored in the memory to perform or control performance of at least one operation to:
    assemble the tomographic model of the target infrastructure based on the analyzed information about the one or more signals.

13. The system according to claim 12, wherein to assemble the tomographic model, the processor is configured to execute the instructions stored in the memory to perform or control performance of at least one operation to:
    extract, from the analyzed information about the one or more signals, channel state data that represent propagation conditions of the one or more signals through the target infrastructure.

14. The system according to claim 13, wherein the extracted channel state data is indicative of effects of one or more of: a multipath, a spatial distribution, and a conductivity of the target infrastructure.

15. The system according to claim 13, wherein to assemble the tomographic model, the processor is configured to execute the instructions stored in the memory to perform or control performance of at least one operation to:
aggregate the extracted channel state data into a density and conductance map of the target infrastructure.

16. The system according to claim 13, wherein the processor is further configured to execute the instructions stored in the memory to perform or control performance of at least one operation to:
update the tomographic model with newly received data from additional one or more pairs of mobile communication devices.

17. The system according to claim 13, wherein the processor is further configured to execute the instructions stored in the memory to perform or control performance of at least one operation to:
employ the tomographic model to detect target infrastructure flaws that include one or more of: material loss, spalling, pop-outs, cracks, honeycombing, corrosion, rusting, and misalignment of bearings and reinforcement structures.

18. A non-transitory computer-readable storage medium having stored thereon computer-executable instructions that, in response to execution, cause a processor to perform or control performance of operations to:
identify a target infrastructure to monitor;
identify a pair of mobile communication devices that approach the target infrastructure;
instruct the pair of mobile communication devices to communicate with each other through one or more signals as the pair of mobile communication devices pass the target infrastructure;
instruct at least one mobile communication device of the pair of mobile communication devices to collect information about the one or more signals;
obtain the collected information about the one or more signals from the at least one mobile communication device of the pair of mobile communication devices;
analyze the collected information about the one or more signals to determine a structural characteristic of the target infrastructure; and
instruct a result of the analysis to be provided to a tomographic data builder, wherein the provided result of the analysis is usable to assemble a tomographic model.

19. The non-transitory computer-readable storage medium according to claim 18, wherein the computer-executable instructions, in response to execution, cause the processor to perform or control performance of at least one operation to:
assemble the tomographic model of the target infrastructure based on the analyzed information about the one or more signals.

20. The non-transitory computer-readable storage medium according to claim 19, wherein the assembly of the tomographic model comprises an extraction, from the analyzed information about the one or more signals, of channel state data that represent propagation conditions of the one or more signals through the target infrastructure.

21. The non-transitory computer-readable storage medium according to claim 20, wherein the assembly of the tomographic model comprises an aggregation of the extracted channel state data into a density and conductance map of the target infrastructure.

22. The non-transitory computer-readable storage medium according to claim 20, wherein the computer-executable instructions, in response to execution, cause the processor to perform or control performance of at least one operation to:
employ the tomographic model to detect target infrastructure flaws that include one or more of: material loss, spalling, pop-outs, cracks, honeycombing, corrosion, rusting, and misalignment of bearings and reinforcement structures.

23. A mobile communication system to monitor roadway infrastructure based on aggregated mobile vehicle communication parameters, the mobile communication system comprising:
at least one storage device; and
at least one server operatively coupled to the at least one storage device and configured to communicate with a plurality of mobile communication devices, wherein the at least one server is configured to:
identify, from information stored in the at least one storage device, a target infrastructure to monitor;
identify a pair of mobile communication devices, among the plurality of mobile communication devices, that approach the target infrastructure;
instruct the pair of mobile communication devices to communicate with each other through one or more signals as the pair of mobile communication devices pass the target infrastructure;
instruct at least a mobile communication device of the pair of mobile communication devices to collect information about the one or more signals;
receive the collected information about the one or more signals from the at least mobile communication device of the pair of mobile communication devices;
analyze the collected information about the one or more signals to determine a structural characteristic of the target infrastructure; and
instruct a result of the analysis to be provided to a tomographic data builder, wherein the provided analysis result is usable to assemble a tomographic model.

24. The system of claim 23, wherein the at least one storage device is configured to store the tomographic data builder and the assembled tomographic model.

25. The system of claim 23, wherein:
the at least one server is configured to operate the tomographic data builder to assemble the tomographic model of the target infrastructure based on the analyzed information about the one or more signals, and
the tomographic builder is configured to extract, from the analyzed information about the one or more signals, channel state data that represent propagation conditions of the one or more signals through the target infrastructure.

* * * * *

UNITED STATES PATENT AND TRADEMARK OFFICE
CERTIFICATE OF CORRECTION

| | |
|---|---|
| PATENT NO. | : 9,784,692 B2 |
| APPLICATION NO. | : 14/372439 |
| DATED | : October 10, 2017 |
| INVENTOR(S) | : Kruglick |

It is certified that error appears in the above-identified patent and that said Letters Patent is hereby corrected as shown below:

In the Specification

In Column 8, Line 29, delete "OPS system," and insert -- GPS system, --, therefor.

In Column 8, Line 45, delete "322, of" and insert -- 322 of --, therefor.

In Column 8, Line 63, delete "UPS, an" and insert -- GPS, an --, therefor.

In Column 10, Line 40, delete "and potential" and insert -- and a potential --, therefor.

In Column 14, Line 4, delete "an/or a" and insert -- and/or a --, therefor.

In Column 14, Line 42, delete "identity a" and insert -- identify a --, therefor.

In Column 16, Line 45, delete "instruct pair" and insert -- instruct the pair --, therefor.

In Column 17, Line 36, delete "where least" and insert -- where at least --, therefor.

In Column 18, Line 57, delete "thereof and" and insert -- thereof, and --, therefor.

In Column 19, Line 67, delete "and/or interactable" and insert -- and/or logically interactable --, therefor.

Signed and Sealed this
First Day of May, 2018

Andrei Iancu
*Director of the United States Patent and Trademark Office*